United States Patent
Yu et al.

(10) Patent No.: US 11,234,707 B2
(45) Date of Patent: Feb. 1, 2022

(54) DISPOSABLE HEMOSTATIC CLIP SYSTEM

(71) Applicant: BEIJING DONGLIN FUSHI MEDICAL DEVICES CO., LTD., Beijing (CN)

(72) Inventors: Ling Yu, Beijing (CN); Chun Yu, Beijing (CN); Yonghui Huang, Beijing (CN)

(73) Assignee: BEIJING DONGLIN FUSHI MEDICAL DEVICES CO., LTD., Beijing (CN)

( * ) Notice: Subject to any disclaimer, the term of this patent is extended or adjusted under 35 U.S.C. 154(b) by 43 days.

(21) Appl. No.: 16/730,874

(22) Filed: Dec. 30, 2019

(65) Prior Publication Data
US 2020/0229823 A1    Jul. 23, 2020

(30) Foreign Application Priority Data

Jan. 22, 2019   (CN) .......................... 201910060262.X
Jan. 22, 2019   (CN) .......................... 201920105830.9

(51) Int. Cl.
*A61B 17/128*    (2006.01)
*A61B 17/122*    (2006.01)
*A61B 17/12*     (2006.01)

(52) U.S. Cl.
CPC .......... *A61B 17/122* (2013.01); *A61B 17/128* (2013.01); *A61B 2017/12004* (2013.01)

(58) Field of Classification Search
CPC ....... A61B 17/08; A61B 17/083; A61B 17/10; A61B 17/12; A61B 17/122; A61B 17/1227; A61B 17/128; A61B 17/1285; A61B 2017/12004; A61B 2017/00831
See application file for complete search history.

(56) References Cited

U.S. PATENT DOCUMENTS

| | | | |
|---|---|---|---|
| 7,727,247 B2 * | 6/2010 | Kimura | A61B 50/30 606/157 |
| 2005/0049618 A1 * | 3/2005 | Masuda | A61B 17/122 606/151 |
| 2007/0293875 A1 | 12/2007 | Soetikno et al. | |
| 2011/0184453 A1 * | 7/2011 | Levy | A61L 31/148 606/195 |

(Continued)

OTHER PUBLICATIONS

Extended European Search Report from corresponding EP app. No. 20151884.2, dated Jun. 26, 2020.

*Primary Examiner* — Melanie R Tyson
(74) *Attorney, Agent, or Firm* — Ladas & Parry, LLP

(57) ABSTRACT

A disposable hemostatic clip is provided, the clip includes two degradable clip-arms, a pulling bracket, a hook handle and a degradable sleeve. The degradable clip-arms are respectively arranged on two front portions of the pulling bracket; a lower part of the pulling bracket hooks with the hook handle; and the pulling bracket and the hook handle are assembled in the degradable sleeve. The degradable clip-arms and the degradable sleeve are made by using a degradable material, so that all the parts of the hemostatic clip retained in the body are degradable. At the same time, the disposable hemostatic clip also provides a metal part used in combination with a degradable part, thereby achieving separation and retention of a degradable clip portion.

7 Claims, 7 Drawing Sheets

(56) References Cited

U.S. PATENT DOCUMENTS

| | | | |
|---|---|---|---|
| 2013/0226200 A1* | 8/2013 | Kappel | A61B 17/1285 606/142 |
| 2016/0120546 A1* | 5/2016 | Roundy | A61B 17/122 606/143 |
| 2018/0125497 A1 | 5/2018 | Cohen et al. | |
| 2019/0231353 A1* | 8/2019 | Saenz Villalobos | A61B 17/1227 |

* cited by examiner

DISPOSABLE HEMOSTATIC CLIP SYSTEM

CROSS-REFERENCE TO RELATED APPLICATION

This application claims priority to Chinese Application No. 201910060262.X filed on Jan. 22, 2019, and Chinese Application No. 201920105830.9 filed on Jan. 22, 2019, the disclosures of which are hereby incorporated by reference in their entireties.

BACKGROUND

Technical Field

The present invention relates to a disposable hemostatic clip system, belonging to the technical field of medical instruments.

Related Art

Laparoscopic surgery began in the 1980. In China, this minimally invasive surgery was introduced in the early 1990s. During the surgery, a hemostatic clip is frequently used clinically to stop bleeding, the operation is relatively easy, and the effect of hemostasis is better. The more commonly used hemostatic clip materials are mainly non-degradable metal materials and degradable polymer hemostatic clips. Both types of hemostatic clips are used clinically, but both have certain problems.

Currently, a titanium alloy hemostatic clip is a commonly used metal hemostatic clip in clinical laparoscopic surgery. Although the hemostatic clip causes little toxin to human body, the permanent retention thereof in the body will cause problems of resulting in ion dissolution inflammation, disturbing the imaging diagnosis, leading to the psychological burden of patients and the like. Although the absorbable polymer hemostatic clip can be degraded in vivo, the mechanical strength of a polymer material is insufficient, resulting in a limited holding time of a clamping force and too high product cost.

In addition, improvements to the degradable hemostatic clips are now being largely focused on improving the material of the hemostatic clip, so that a structural design used in conjunction with a degradable material is in need.

SUMMARY

The technical problem to be solved by the present invention is to provide a disposable hemostatic clip system.

In order to achieve the above technical purpose, the present invention adopts the following technical solutions:

A disposable hemostatic clip system, comprising two degradable clip-arms, a pulling bracket, a hook handle and a degradable sleeve, wherein the degradable clip-arms are respectively arranged on two front portions of the pulling bracket; a lower part of the pulling bracket hooks with the hook handle; and the pulling bracket and the hook handle are assembled in the degradable sleeve, the two degradable clip-arms each have a long groove for accommodating the respective front portion of the pulling bracket, and a connecting post for coupling with a corresponding hole in the front portions of the pulling bracket.

Preferably, the degradable clip and the degradable sleeve are made of Poly-L-lactic acid, and the Poly-L-lactic acid has molecular weight of more than 220,000.

Preferably, the long groove has a depth equal to the thickness of the pulling bracket.

Preferably, the pulling bracket has a left side bracket and a right side bracket which are symmetrical to each other, and the lower part of the pulling bracket is bent to form a connecting hook, the left side bracket and the right side bracket respectively bending outwardly from the lower part of the pulling bracket to form an arc, returning to cross with each other at a middle portion, and extending upwardly from the middle portion to form a front portion for being embedded in the long groove.

Preferably, between the middle portion and the front portion, the left side bracket and the right side bracket respectively forms an outwardly protruding arc, the arc having an outermost side which are coplanar with an outer side wall of the degradable clip, whose heights are substantially equal.

Preferably, the degradable sleeve has a limiting groove in an inner wall thereof; the degradable clip has a protruding limiting strip on an outer side wall thereof close to the degradable sleeve.

Preferably, the circlip has a plurality of connecting claws, each connecting claw sequentially passes through openings arranged in the second sleeve and corresponding openings in the degradable sleeve, so as to connect the degradable sleeve with the second sleeve.

Preferably, the hook handle connects to a control line and passes through a center hole of the circlip.

Preferably, the rear end of the second sleeve is fixed to an end of a spring tube.

According to the disposable hemostatic clip system provided by the present invention, a degradable clip and a degradable sleeve are produced by using a degradable material, so that the portions of the hemostatic clip retained in the body are all degradable. At the same time, the disposable hemostatic clip system also provides a metal part used in combination with the degradable part, and the mechanical strength of the hemostatic clip is improved while the hemostatic clip is released, so that the practicability of the hemostatic clip is greatly improved.

DETAILED DESCRIPTION

The technical solutions of the present invention are further described in detail below in combination with the accompanying drawings and specific embodiments.

The disposable hemostatic clip system provided by the present invention is made of a degradable material (for example, a biomedical material PLLA (Poly-L-lactic acid)) combined with a metal material (for example, a stainless steel material). The clip portion, for being retained in the body, of the disposable hemostatic clip is made of a degradable material, and other parts that are not retained in the body can be made of a metal material. The metal parts are used to enhance the mechanical strength of the hemostatic clip.

Figure 1:
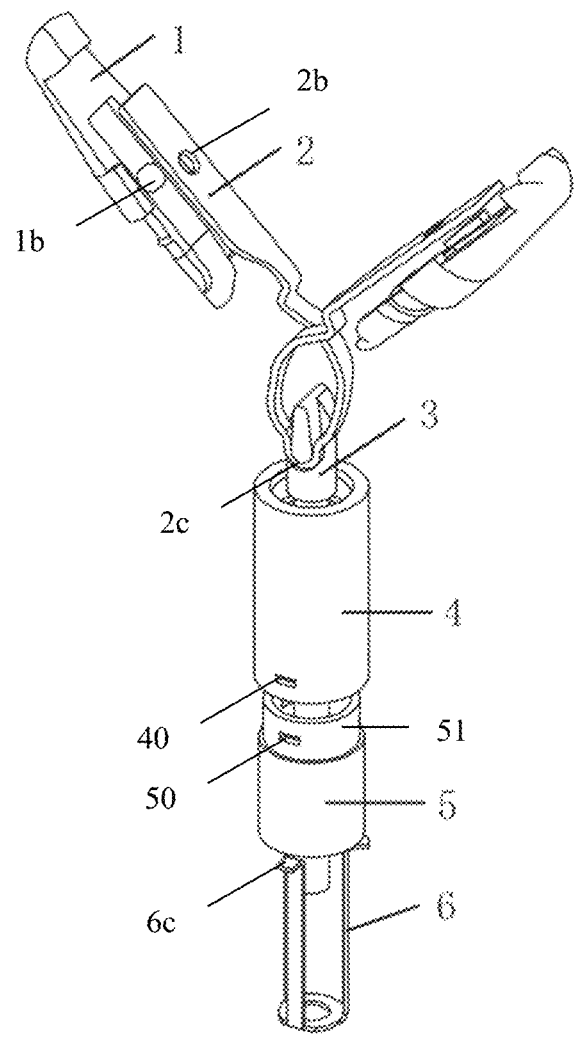
FIG. 1 is an exploded view of a disposable hemostatic clip system provided by the present invention.

Specifically, as shown in FIG. 1, the disposable hemostatic clip system provided by the present invention comprises two degradable clip-arms 1, a pulling bracket 2, a hook handle 3, a degradable sleeve 4, a second sleeve 5, a circlip 6, a control handle and accessories for being used in cooperation with the control handle.

The two degradable clip-arms 1 and the degradable sleeve 4 constitute a clip portion 10 (see FIG. 8) for being finally retained in the body, both of which are made of degradable materials. For example, both can be made of a PLLA material, which is a degradable material that has been approved by the CFDA to be widely used in human body. In the present invention, the PLLA material used to make the degradable clip 1 and the degradable sleeve 4 has a molecular weight of more than 220,000. The mechanical strength of the PLLA material is increased by increasing the molecular weight to ensure a certain clamping force when soft tissue and blood vessels are clamped. Although increasing the molecular weight will delay the complete degradation time of PLLA, since the PLLA material will eventually be completely degraded, it is resolved that the non-degradable materials retained in the body due to the non-degradable titanium clip or the like cause other adverse reactions during some current endoscopic treatment. Of course, the two degradable clip-arms 1 and the degradable sleeve 4 can also be made of other degradable materials suitable for biomedical use.

The two degradable clip-arms 1 provided by the present invention have identical or mutually symmetrical structures. When the two degradable clip-arms 1 are locked inside the degradable sleeve 4, the target soft tissues or target blood vessels can be clamped between the two degradable clip-arms 1.

Figure 2A:
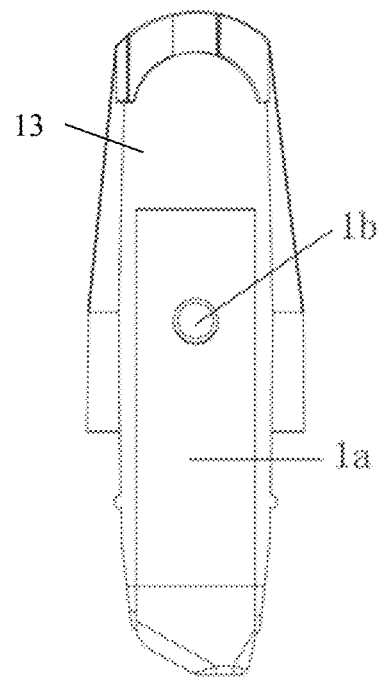
FIG. 2A and FIG. 2B are schematic front view and schematic side view of a degradable clip respectively.
Figure 2B:
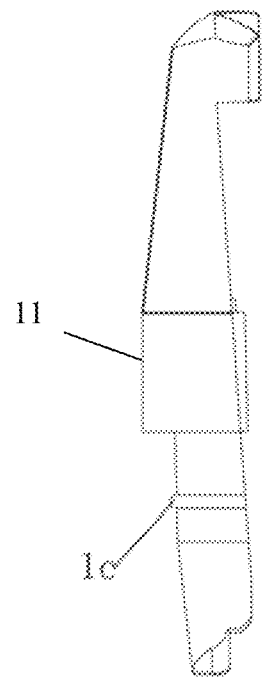

As shown in FIG. 2A and FIG. 2B, a long groove 1a for accommodating the front portion 2a of the pulling bracket 2 is arranged on a facing side (i.e. the side being facing each other and used for clamping) of each of the two degradable clip-arms 1. The depth of the long groove 1a is equal to the thickness of the pulling bracket 2, so that after the pulling bracket 2 is embedded into the long groove 1a, the adjacent portions of the long groove 1a together with the pulling bracket 2 form a smooth surface 13 (see FIG. 6) to avoid accidental damage to the target soft tissues or target blood vessels. A protruding connecting post 1b is provided in the long groove 1a, and the connecting post 1b and the degradable clip-arms 1 are integrated. The connecting post 1b is used to be matched with the connecting hole 2b provided in the front portion 2a of the pulling bracket 2, so as to connect the pulling bracket 2 to the degradable clip-arms 1. An outwardly projecting limiting strip 1c is arranged on the side wall of the outer side (the side close to the degradable sleeve 4) of the degradable clip 1 to be matched with a limiting groove 4a in the inner wall of the degradable sleeve 4, so as to realize the locking function of the clip portion 10.

Figure 7:
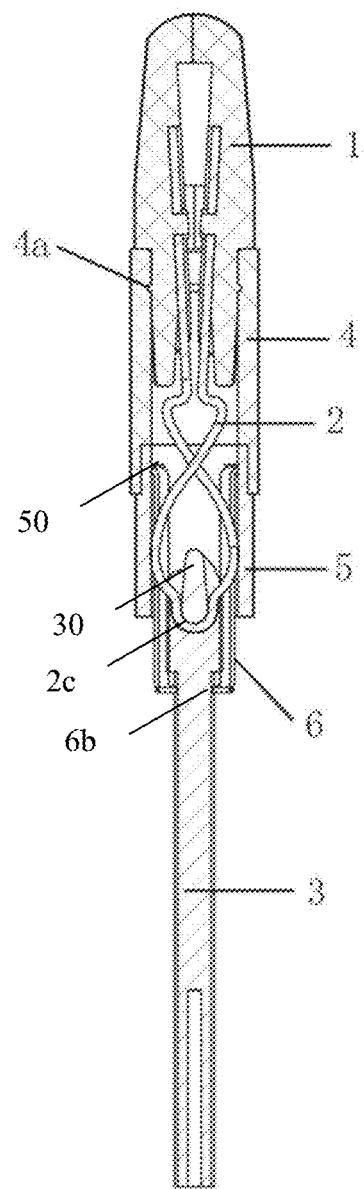
FIG. 7 is a schematic view showing a state in which the degradable clip is closed and locked.

The degradable sleeve 4 is a section of circular tube made of the degradable material PLLA; and the limiting groove 4a is arranged in the inner wall of the degradable sleeve 4. The limiting groove 4a is used for being matched with the limiting strip 1c arranged in the outer side wall 11 of the degradable clip 1, to realize the locking function. As shown in FIG. 7, the degradable clip 1 is pulled into the degradable sleeve 4 by the pulling bracket 2, and the limiting strip 1c is embedded into the limiting groove 4a to lock the degradable clip 1. The rear portion 41 of the degradable sleeve 4 is provided with a thin wall to be inserted with the front portion 51 of the second sleeve 5. A row of openings 40 of equal height is formed in the thin wall at the rear portion 41 of the degradable sleeve 4 to achieve the connection with the second sleeve 5.

Other parts used in cooperation with the above-mentioned degradable clip portion 10 are described below. All of the pulling brackets 2, the hook handle 3, the second sleeve 5 and the circlip 6 are all of stainless steel material. The degradable clip 1 is provided with the pulling bracket 2 and the hook handle 3 made of stainless steel material, so as to provide a mechanical support for the degradable clip 1, and to pull the degradable clip 1 to move, thereby realizing the closure and lock separation of the two degradable clip-arms 1.

Figure 3:
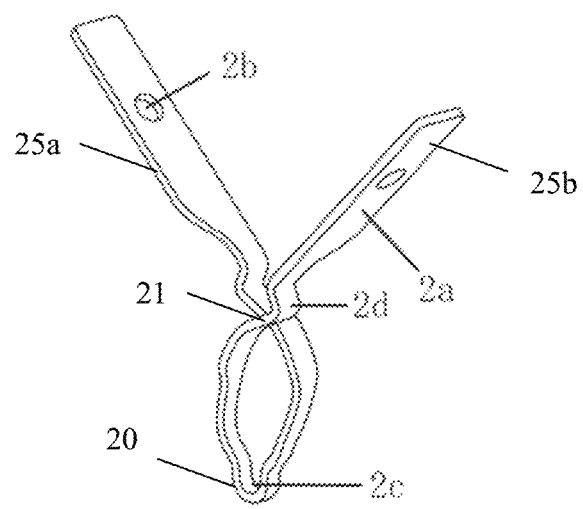
FIG. 3 is a schematic structural view of a pulling bracket.

As shown in FIG. 3, the pulling bracket 2 is an integral elastic bracket formed by twisting and deforming one metal piece, and substantially has a shape of "8". The pulling bracket 2 has two parts, a left side bracket 25a and a right side bracket 25b, which are bilaterally symmetrical to each other. The lower part 20 of the pulling bracket 2 is bent into a connecting hook 2c. The left side bracket 25a and the right side bracket 25b are respectively bent outside from the connecting hook 2c of the pulling bracket 2 to respectively form an arc, then returned inside to the middle portion 21 to be crossed with each other, and continue to extend upward to respectively form a front portion 2a to be embedded in the long groove 1a. A connecting hole 2b is formed in each front portion 2a of the pulling bracket 2. The connecting holes 2b are used to be matched with the corresponding connecting posts 1b, thereby fixing the degradable clip-arms 1 to the corresponding front portions 2a of the pulling bracket 2. Further, an outwardly protruding arc 2d is respectively formed at the portion where the left side bracket 25a and the right side bracket 25b respectively extend to the front portions 2a upper than the middle portion 21 that the left side bracket 25a and the right side bracket 25b cross each other. The outermost side of the arc 2d and the outer side wall 11 of the degradable clip 1 are coplanar, whose height are substantially equal, when the degradable clip 1 is installed at the front portion 2a of the pulling bracket 2, so that the degradable clip 1 can enter the degradable sleeve 4 smoothly during movement of the pulling bracket 2.

Figure 4:
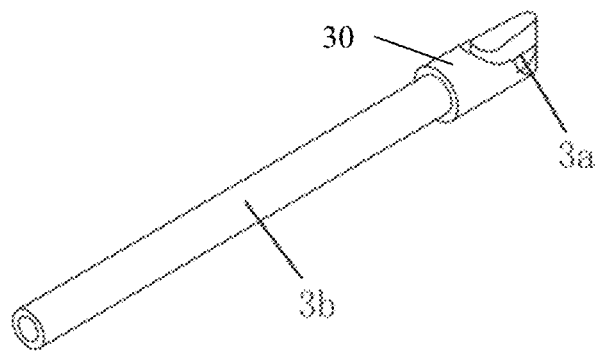
FIG. 4 is a schematic structural view of a hook handle.

As shown in FIG. 4, the front portion 30 of the hook handle 3 has a larger diameter than that of the connecting rod 3b, and is provided with a hook-shaped groove 3a for matching with the hook shape of the connecting hook 2c. The pulling bracket 2 is hooked with the hook handle 3 when the connecting hook 2c at the lower part 20 of the pulling bracket 2 edges into the hook-shaped groove 3a at the front portion 30 of the hook handle 3. The rear portion of the hook handle 3 is cylindrical connecting rod 3b. The hook handle 3 is connected with a control wire by the means of inserting and fixing the control wire from the tail end of the hook handle 3 to the connecting rod 3b.

The second sleeve 5 is a circular tube. The front portion 51 of the second sleeve 5 is a wall which is thinned from the outside, so that the outer diameter of the thin wall at the front portion 51 of the second sleeve 5 is equal to the inner diameter of the thin wall at the rear portion 41 of the degradable sleeve 4. A circle of openings 50 of equal height is provided on the thin wall at the front portion 51 of the second sleeve 5, and the openings 50 provided at the front portion 51 of the second sleeve 5 correspond to the openings 40 provided at the rear portion 41 of the degradable sleeve 4.

Figure 5A:
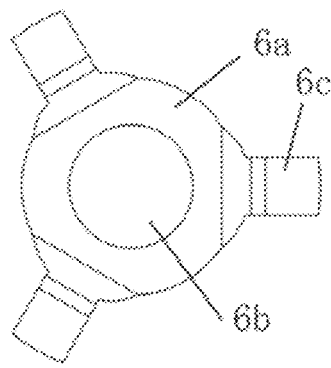
FIG. 5A and FIG. 5B are schematic top view and schematic front view of a circlip respectively.
Figure 5B:
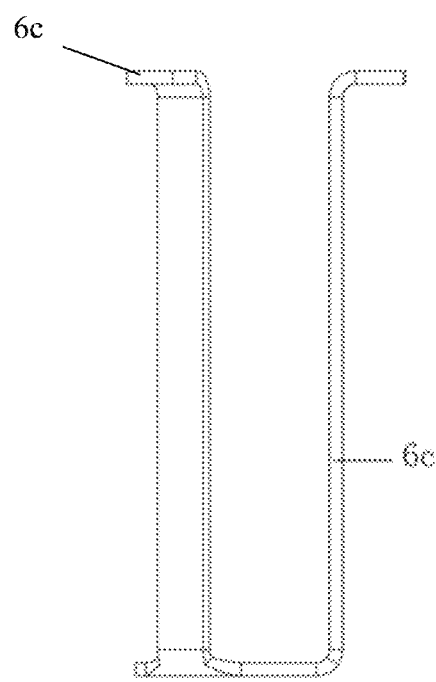

The circlip 6 as shown in FIG. 5 is composed of a ring portion 6a and a plurality of connecting claws 6c integrated with the ring portion 6a. A center hole 6b is formed at the center of the ring portion 6a, and the connecting claws 6c are evenly arranged on the outer circumference of the ring portion 6a. The second sleeve 5 is connected with the degradable sleeve 4 when the connecting claws 6c are sequentially inserted into the openings 50 in the second sleeve 5 and the openings 40 correspondingly provided in the degradable sleeve 4. In this embodiment, the circlip 6 is provided with three connecting claws 6c, and three openings (40, 50) corresponding to the connecting claws 6c are respectively arranged on the degradable sleeve 4 and the second sleeve 5. The order of which the connecting claws 6c are inserted into the degradable sleeve 4 and the second sleeve 5 may be reversed, depending on the structure of the degradable sleeve 4 and the second sleeve 5. At the time of connecting the degradable sleeve 4 with the second sleeve 5, the degradable sleeve 4 with the second sleeve 5 are first fastened together, and then the connecting claws 6c of the circlip 6 are inserted into the corresponding openings (40, 50) so as to complete the connection of the degradable sleeve 4 with the second sleeve 5. After the degradable sleeve 4 and the second sleeve 5 are connected, the rear portion 3b of the hook handle 3 passes through the center hole 6b of the circlip 6 and is connected to the control wire. The diameter of the center hole 6b is larger than the diameter of the connecting rod 3b at the rear portion of the hook handle 3, but smaller than the diameter of the front portion 30 of the hook handle 3. If the hook handle 3 is pulled backward so that the front portion 30 of the hook handle 3 acts on the center hole 6b of the circlip 6, the circlip 6 is forced to deform, thereby the connecting claws 6c of the circlip 6 being constrained, and thus the degradable sleeve 4 and the second sleeve 5 are disconnected.

The assembly process of the disposable hemostatic clip system provided by the present invention is described below.

At the time of assembling the disposable hemostatic clip system, firstly, the two degradable clip-arms 1 are installed at the front portion of the pulling bracket 2, and the lower part 20 of the pulling bracket 2 is hooked with the front portion 30 of the hook handle 3. Secondly, the degradable sleeve 4 and the second sleeve 5 are inserted together, and then are fixed together by the circlip 6. Thirdly, the hook handle 3 is passed through the center hole 6b of the circlip 6 and then connected to the control line. Finally, the circlip 6 is connected to the second sleeve 5 to complete the assembly process of the disposable hemostatic clip system.

Figure 6:
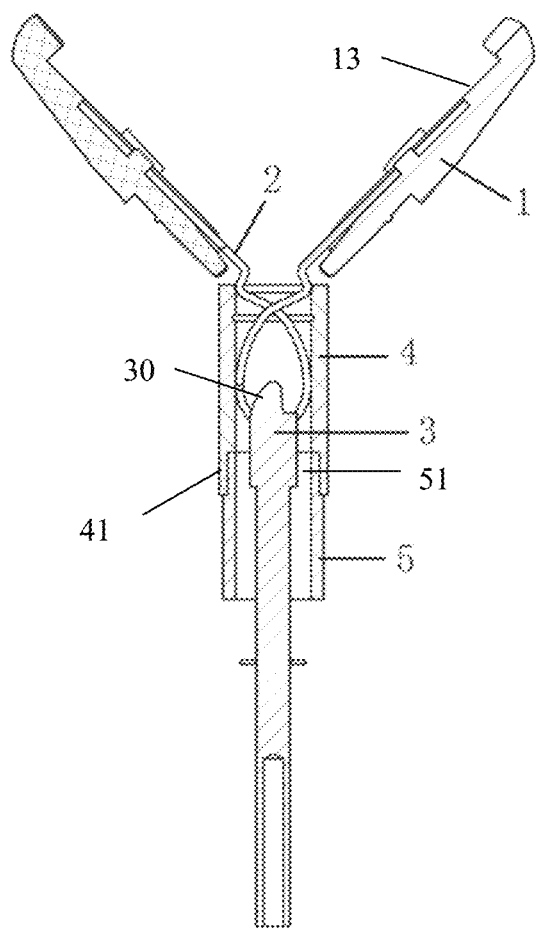
FIG. 6 is a schematic structural view of the assembled disposable hemostatic clip system.

As described above, the disposable hemostatic clip system provided by the present invention has a structure as shown in FIG. 6 when not in use. Two degradable clip-arms 1 are respectively fixed at the front portion of the pulling bracket 2, and the connecting hook 2c of the pulling bracket 2 is hooked to the hook-shaped groove 3a of the hook handle 3. The degradable sleeve 4 and the second sleeve 5 cover the outside of the pulling bracket 2 and the hook handle 3. The degradable sleeve 4 and the second sleeve 5 are assembled together by the circlip 6. The rear portion of the hook handle 3 is connected to the control line and passes through the center hole 6b the circlip 6. The control wire passes through the spring tube and is connected to a control knob on the control handle (not showing). The rear end of the second sleeve 5 is fixed to one end of the spring tube, and the other end of the spring tube is fixed to the housing of the control handle. Due to an arranged positioning block mechanism on the control handle, the degradable clip 1 can only partially enter the degradable sleeve 4 so that the clip portion assumes a closed initial state. The degradable clip 1 can also be opened and closed again when a bracelet connected to the hook handle 3 is pushed.

Figure 8:
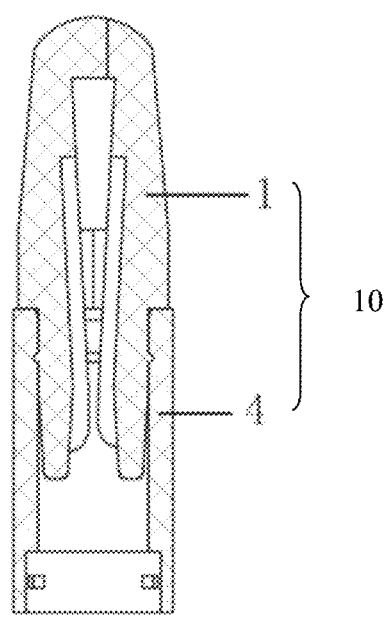
FIG. 8 is a schematic view showing the structure of a degradable portion retained in the body.

In the process of use, the hook handle 3 is pulled backward so as to pull the pulling bracket 2. Consequently, the two degradable clip-arms 1 are driven into the degradable sleeve 4. Then the two degradable clip-arms 1 are closed, so that the two degradable clip-arms 1 are locked inside the degradable sleeve 4 (as shown in FIG. 7). Subsequently, the hook handle 3 is continuously pulled backward, and the pulling bracket 2 is driven by the hook handle 3 to break the connecting post 1b, and thus the pulling bracket 2 is separated from the degradable clip 1. The hook handle 3 is continuously pulled, the circlip 6 is forced by the hook handle 3 to deform, and the three connecting claws 6c of the circlip 6 retreat so as to retract from the openings 40 of the degradable sleeve 4, thereby separating the second sleeve 5 from the degradable sleeve 4. Thus, the degradable clip 1 and the degradable sleeve 4 as shown in FIG. 8 are retained in the body, the rest made of a metal material (including the pulling bracket 2, the hook handle 3, the second sleeve 5, and the circlip 6) are withdrawn from the body through the channel of biopsy forceps of endoscope along with the spring tube and the control line (not showing).

In summary, a disposable hemostatic clip system provided by the present invention comprises a degradable clip and a degradable sleeve made of a degradable material, so that the clip portion retains in the body can be degraded. At the same time, metal parts used in combination with the degradable part are also provided. The present invention realizes the separation and retention of the degradable clip portion, improves the mechanical strength of the disposable hemostatic clip system during operation, and thus greatly improves practicability of the hemostatic clip system.

The disposable hemostatic clip system provided by the present invention are described in detail above. For those of ordinary skill in the art, any obvious changes made to the present invention is included in the present invention, and will constitutes an infringement of the patent right of the present invention and bear corresponding legal liabilities.

What is claimed is:

1. A disposable hemostatic clip system, comprising two degradable clip-arms, a pulling bracket, a hook handle and a degradable sleeve, wherein the two degradable clip-arms are respectively arranged on two front portions of the pulling bracket; a lower part of the pulling bracket hooks with the hook handle; and the pulling bracket and the hook handle are assembled in the degradable sleeve, wherein
   the two degradable clip-arms each have a long groove for accommodating the respective front portion of the pulling bracket, and a connecting post for coupling with a corresponding hole in the front portions of the pulling bracket.

2. The disposable hemostatic clip system according to claim 1, wherein
   the two degradable clip-arms and the degradable sleeve are made of Poly-L-lactic acid, and the Poly-L-lactic acid has molecular weight of more than 220,000.

3. The disposable hemostatic clip system according to claim 1, wherein
   the long grooves each have a depth equal to a thickness of the pulling bracket.

4. The disposable hemostatic clip system according to claim 1, wherein the pulling bracket has a left side bracket and a right side bracket which are symmetrical to each other, and the lower part of the pulling bracket is bent to form a connecting hook, the left side bracket and the right side bracket respectively bending outwardly from the lower extending upwardly from the middle portion to form the front portions for being embedded in the respective long groove.

5. The disposable hemostatic clip system according to claim 4, wherein arcs are located respectively between the middle portion and the front portion of the left side bracket and the right side bracket;

the arcs each have an outermost side which is coplanar with an outer side wall of a respective one of the two degradable clip-arms.

6. The disposable hemostatic clip system according to claim 1, wherein the degradable sleeve has a limiting groove in an inner wall thereof;

the two degradable clip-arms each have a protruding limiting strip on an outer side wall thereof close to the degradable sleeve.

7. The disposable hemostatic clip system according to claim 1, further comprising a circlip and a second sleeve, wherein the circlip has a plurality of connecting claws, each connecting claw sequentially passes through openings arranged in the second sleeve and corresponding openings in the degradable sleeve, so as to connect the degradable sleeve with the second sleeve.

* * * * *